US00PP27016P2

(12) United States Plant Patent
Dofferhoff

(10) Patent No.: US PP27,016 P2
(45) Date of Patent: Aug. 2, 2016

(54) ***GENTIANA* PLANT NAMED 'BLUE STAR'**

(50) Latin Name: *Gentiana makinoi*
Varietal Denomination: Blue Star

(71) Applicant: Hans Dofferhoff, Reeuwijk (NL)

(72) Inventor: Hans Dofferhoff, Reeuwijk (NL)

(73) Assignee: KWEKERIJ DE BOEZEM B.V., Reeuwijk (NL)

( * ) Notice: Subject to any disclaimer, the term of this patent is extended or adjusted under 35 U.S.C. 154(b) by 188 days.

(21) Appl. No.: 13/999,794

(22) Filed: Mar. 21, 2014

(51) Int. Cl.
*A01H 5/02* (2006.01)

(52) U.S. Cl.
USPC ..... Plt./433

(58) Field of Classification Search
USPC ..... Plt./263.1, 433
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Gentiana makinoi* plant named 'Blue Star' that is characterized by its upright and globular plant habit, its violet-blue flowers, its free flowering plant habit, and its long bloom period lasting for 8 to 12 weeks from mid-July to mid-September in The Netherlands.

2 Drawing Sheets

Botanical classification: *Gentiana makinoi.*
Varietal denomination: 'Blue Star'.

BACKGROUND OF THE INVENTION

The present invention relates to a new and distinct cultivar of *Gentiana makinoi* and will be referred to hereafter by its cultivar name, 'Blue Star'. 'Blue Star' represents a new Gentian, an herbaceous perennial grown for landscape use.

The inventor discovered the new cultivar, 'Blue Star', as a naturally occurring whole plant mutation in a nursery plot of *Gentiana makinoi* 'Marsha' (U.S. Plant Pat. No. 16,562) in Reeuwijk, The Netherlands in 2010.

Asexual propagation of the new cultivar was first accomplished under the direction of the Inventor by in vitro propagation in Reeuwijk, The Netherlands in May of 2011. Asexual propagation by stem cuttings and tissue culture has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Blue Star' as a new and unique cultivar of *Gentiana.*

1. 'Blue Star' exhibits a broad upright, globular plant habit.
2. 'Blue Star' exhibits violet-blue flowers.
3. 'Blue Star' exhibits a free flowering plant habit.
4. 'Blue Star' exhibits a long bloom period lasting for 8 to 12 weeks from mid-July to mid-September in The Netherlands.

'Marsha', the parent plant of 'Blue Star', differs from 'Blue Star' in being larger in size and in having a shorter bloom period. 'Blue Star' can be most closely compared to the *Gentiana* cultivars 'Blue Rock' (U.S. Plant Pat. No. 16,619), 'Blue Magic' (U.S. Plant Pat. No. 20,704) and 'White Magic' (U.S. Plant Pat. No. 21,759). 'Blue Rock' differs from 'Blue Star' in having flowers that are light blue in color and in having a later bloom season that begins in mid August. 'Blue Magic' differs from 'Blue Star' in having flowers that are light blue in color and in having an earlier bloom season that begins in June. 'White Magic' differs from 'Blue Star' in having a shorter plant height and in having white flowers.

BRIEF DESCRIPTION OF THE DRAWINGS

The accompanying colored photographs illustrate the overall appearance and distinct characteristics of the new *Gentiana*. The photographs were taken of plants 18 months in age as field grown in Reeuwijk, The Netherlands (placed in a container for the photographs).

Figure 1:
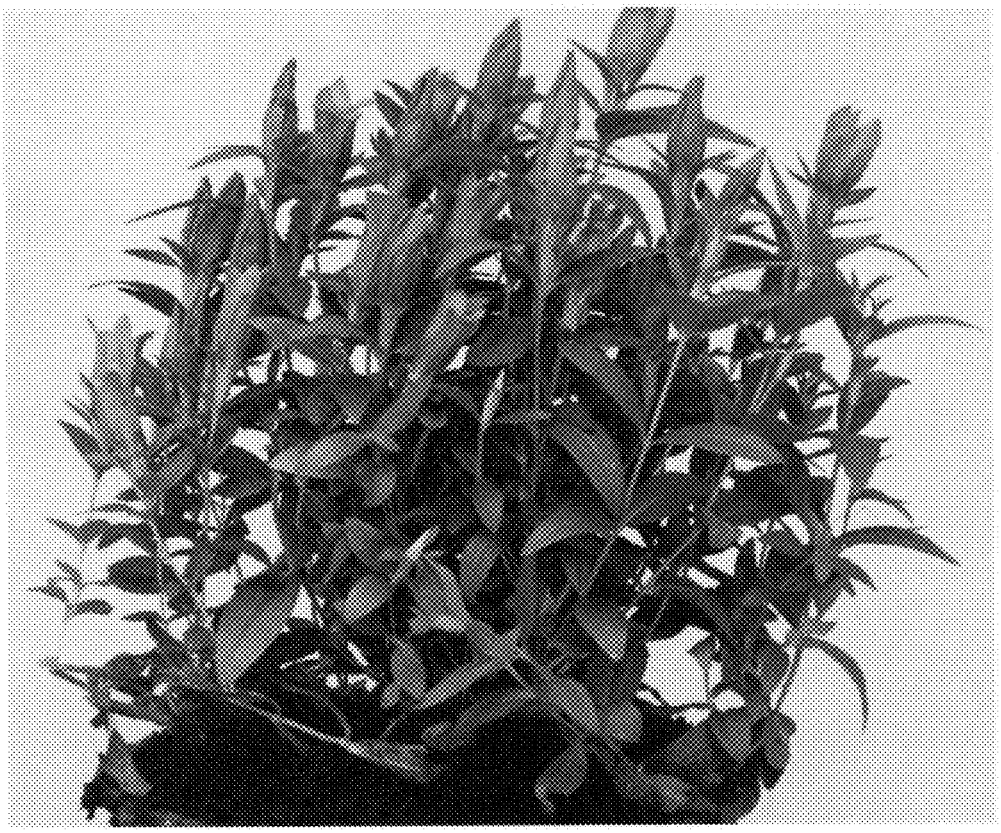
FIG. 1 provides a side view of the plant habit of 'Blue Star' in bloom.
Figure 2:
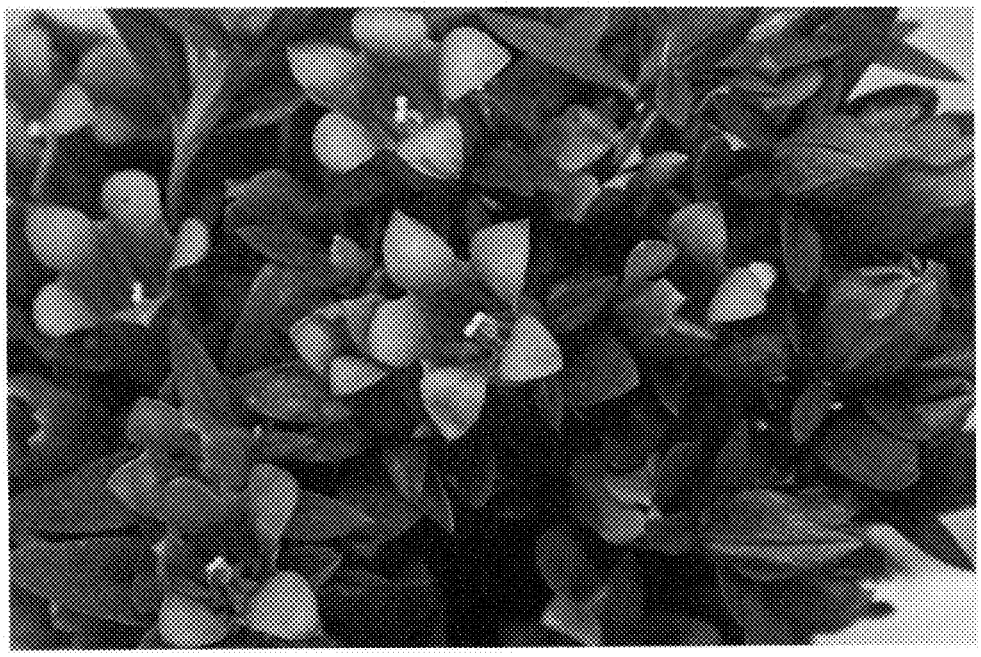

The photograph in FIG. 2 provides a close-up view of the flowers of 'Blue Star'.

Figure 3:
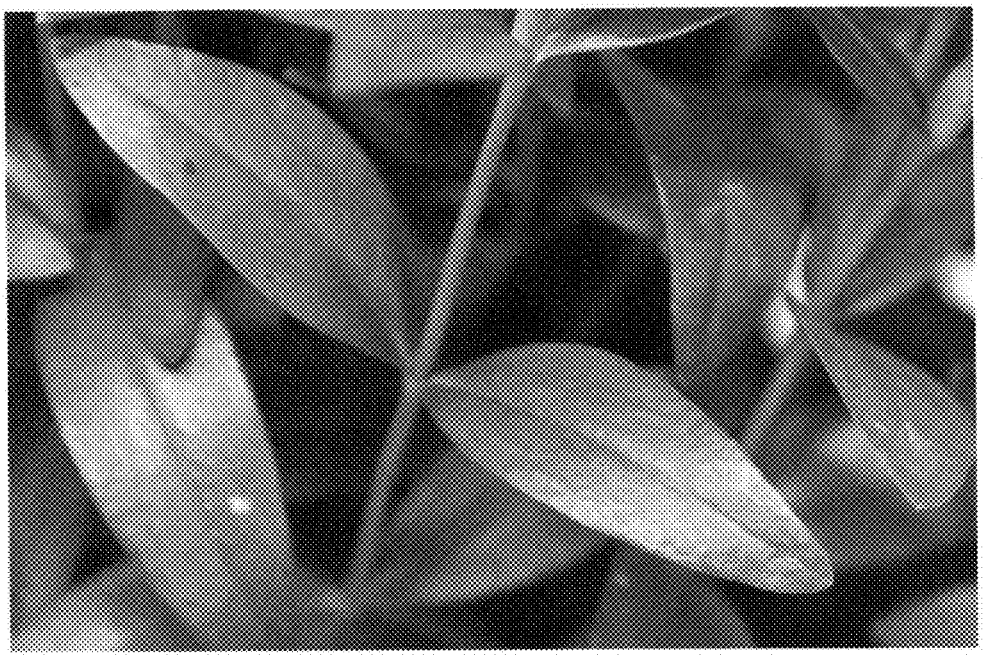

The photograph in FIG. 3 provides a close-up view of the foliage of 'Blue Star'.

The colors in the photographs are as close as possible with the photographic and printing technology utilized and the color values cited in the detailed botanical description accurately describe the colors of the new *Gentiana.*

DETAILED BOTANICAL DESCRIPTION OF THE PLANT

The following is a detailed description of 18 month-old plants of the new cultivar as field grown in Reeuwijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Long blooming; blooming continuously from mid-July to mid-September in The Netherlands.

*Plant type*.—Herbaceous perennial.

*Plant habit*.—Upright, globular.

*Height and spread*.—An average of 24.5 cm in height and spread.

*Cold hardiness*.—At least to U.S.D.A. Zone 6.

*Diseases and pests*.—No unique susceptibility or resistance to diseases or pests has been observed.

*Root description*.—Fine and fibrous.

*Propagation type*.—Stem cuttings and tissue culture.

*Growth rate*.—Moderate.

Stem description:

*Stem shape*.—Rounded.

*Stem color*.—143B.

*Stem size*.—An average of 11 cm in length and 3 mm in diameter.

*Stem surface*.—Slightly glossy and glabrous.

*Stem aspect*.—Main stems held horizontal (0°) to upright (90°) and lateral stems held at an average angle of 85° to horizontal.

*Internode length*.—An average of 2.4 cm.

*Branching habit*.—An average of 6 main basal stems and 9 lateral branches per main stem.

Foliage description:

*Leaf shape*.—Elliptic to ovate, slightly reflexed.

*Leaf division*.—Simple.

*Leaf base*.—Cuneate.

*Leaf apex*.—Acute.

*Leaf venation*.—Pinnate, only the mid ribs on both surfaces are slightly conspicuous, leaf aspect is concave in respect to the mid rib on the upper surface, color; upper surface, N137B and lower surface, 146B to 146C.

*Leaf margins*.—Entire.

*Leaf attachment*.—Sessile.

*Leaf arrangement*.—Opposite.

*Leaf surface*.—Upper and lower surface; glossy and slightly coriaceous.

*Leaf color*.—Immature leaves; upper surface 143A and lower surface 143B, mature leaves; upper surface N137B and lower surface 147B.

*Leaf number*.—Average of 12 (6 pairs) per lateral branch.

*Leaf size*.—Average of 4.1 cm in length and 1.5 cm in width.

Flower description:

*Flower type*.—Axillary and terminal tubular flowers, solitary or in pairs.

*Flower fragrance*.—Faint, lightly cinnamon scented.

*Flower lastingness*.—Average of 10 days on plant, persistent.

*Flowering sequence*.—Flowering on terminus and axillary nodes is primarily simultaneous.

*Flower bud description*.—Narrowly elliptic in shape, average of 1.6 cm in diameter (including sepals), 0.6 cm in diameter (excluding sepals) and 3.5 mm in length, color; petal portion 96B with apex 96A, calyx portion 144C with tips of immature sepals 143A.

*Flower quantity*.—An average of 2 per stem.

*Flower aspect*.—Held upright.

*Flower shape*.—Tubular with 25% of flower open near the apex.

*Flower size*.—An average of 4.3 cm in depth, 2.5 cm in diameter.

*Peduncles*.—An average of 2 mm in length and 1 mm in width, held upright relative to stem, strong, 143C in color.

*Pedicels*.—None present.

*Petal description*.—5, oblong in shape, an average of 3.2 cm in length and 9 mm in width, 75% of lower portion is fused into a tubular shape, corolla lobes are reflexed, margin is entire, apex is acute, upper and lower surface is glabrous and slightly glossy in appearance, color opening and fully open upper surface; 96C, color opening and mature lower surface; a blend between 94A and 96A, both petal surfaces fade to 93A, spots are absent on all surfaces of the corolla.

*Paracorolla*.—Absent.

*Calyx form*.—Campanulate and rotate.

*Sepals*.—An average of 6, average of 2.6 cm in length and 4 mm in width, linear in shape, margin is entire, apex is narrowly acute, base is cuneate with a fused lower half, upper and lower surface is smooth and dull, color immature upper and lower surface; basal half 144C and apical half 143A, color mature upper surface; basal half 144C and apical half N137B, color mature lower surface; basal half 144C and apical half 147B.

Reproductive organs:

*Gynoecium*.—1 pistil an average of 2 mm in length, stigma is decurrent and 150D in color, style is an average of 1 mm in length and 145B in color, ovary is a color between 143C to 144B.

*Androecium*.—5 stamens, anthers are oblong in shape, basifixed, an average of 2.5 mm in length and 6D in color, filaments; an average of 1.3 cm in length and NN155C in color with the lower half implanted in the petal 145B in color, pollen is moderate to high in quantity and 9B in color.

*Fruit*.—No fruit has been observed to date.

It is claimed:

1. A new and distinct cultivar of *Gentiana* plant named 'Blue Star' as herein illustrated and described.

* * * * *